United States Patent [19]

Bissbort et al.

[11] Patent Number: 5,545,670

[45] Date of Patent: Aug. 13, 1996

[54] COMPOSITION AND METHOD FOR THE TREATMENT OF CHRONIC FATIGUE SYNDROME

[76] Inventors: Siegbert H. Bissbort, 387 24th Avenue, Villieria, Pretoria, Transvaal Province; Henry J. Davis, Plot 120, Swavelpoort, Pretoria, Transvaal Province, both of South Africa

[21] Appl. No.: 255,825

[22] Filed: Jun. 8, 1994

Related U.S. Application Data

[63] Continuation of Ser. No. 942,925, Sep. 10, 1992, abandoned.

[30] Foreign Application Priority Data

| Sep. 13, 1991 | [ZA] | South Africa | 91/7333 |
| Sep. 13, 1991 | [ZA] | South Africa | 91/7334 |
| May 20, 1992 | [ZA] | South Africa | 92/3667 |

[51] Int. Cl.$^6$ ............ A61K 31/195; A61K 31/495; A61K 31/44; A61K 31/70; A61K 33/14; A61K 33/10

[52] U.S. Cl. ............ 514/562; 514/249; 514/345; 514/52; 424/681; 424/686

[58] Field of Search .................... 514/562, 249, 514/345, 52; 424/681, 686

[56] References Cited

U.S. PATENT DOCUMENTS

| 4,237,118 | 12/1980 | Howard | 424/630 |
| 4,871,718 | 10/1989 | Carniglia | 514/23 |
| 4,885,157 | 12/1989 | Fiaschetti | 424/59 |
| 4,927,850 | 5/1990 | Bayless et al. | 514/458 |
| 5,055,296 | 10/1991 | Wogle et al. | 424/553 |
| 5,084,482 | 1/1992 | Hirsch et al. | 514/562 |
| 5,132,113 | 7/1992 | Lucá | 424/195.1 |

FOREIGN PATENT DOCUMENTS

| 0018550 | 11/1980 | European Pat. Off. . |
| 0088016 | 9/1983 | European Pat. Off. . |
| 0259167 | 3/1988 | European Pat. Off. . |
| 2126134 | 10/1972 | France . |
| 3707127 | 9/1988 | Germany . |
| 1476615 | 6/1977 | United Kingdom . |
| WO91/07954 | 6/1991 | WIPO . |

OTHER PUBLICATIONS

Cox et al., *Biological Abstracts*, vol. 92, No. 1, abstract No. 08465, 1991, p. 900.
Newberne, *Chemical Abstracts*, vol. 87, No. 9 (66904a), 1977.
Scott et al., *Biological Abstracts*, vol. 73(2), #12119, 1982.
Loo et al., *Chemical Abstracts*, vol. 105(9), #77878m, 1986.
Pristoupilova et al., *Chemical Abstracts*, vol. 105(23), #206642f, 1986.
Shane et al., *Medline*, AN85280090, 1985.
Dialog Information Services, "Methionine a cell chemical immunostimulator", Ciotaru et al., Biosis 1969 1969–1993, Accession No. 7457100 (Abstract), 1989.
C. R. Acad. Sc., "Nutrition et pathologie experimentale", Gaudin–Harding et al., Serie D, vol. 274, No. 10, 1972.
Immunology, "The effect of dietary amino acids on immune reactivity", Bounous et al., vol. 35, No. 2, 1978.
Ann. New York Acad. Sci., "Methionine and the control of creatine biosynthesis", Cohen et al., vol. 494, 1985.
Rote List Bundesvrband der Pharmazeutische Ind., 81, 086, 1986.
Chemical Abstracts, Khannaet al., vol. 96, No. 96:155200W, 1982.
Merck Index, p. 5901, No. 5896, 1989.
Chemical Abstracts, Iemori et al., vol. 92, No. 92:220692s, 1980.

*Primary Examiner*—Marianne M. Cintins
*Assistant Examiner*—William R. A. Jarvis
*Attorney, Agent, or Firm*—Curtis, Morris & Safford, P.C.

[57] ABSTRACT

This invention relates to a composition and method for the treatment of myalgic encephalomyelitis known as chronic fatigue syndrome. The composition consists essentially of specific amounts of L-methionine, magnesium salts, folic acid, vitamin $B_6$, and vitamin $B_{12}$.

6 Claims, 1 Drawing Sheet

FIG.1

COMPOSITION AND METHOD FOR THE TREATMENT OF CHRONIC FATIGUE SYNDROME

This application is a continuation of 07/942,925, filed Sep. 10, 1992, now abandoned.

THIS INVENTION relates to a substance or composition for use in a method of treatment of human and animal subjects to enhance the methylation capacity of such subjects, to enhance or stimulate the immune response system of such subjects, to combat viral infections in such subjects, and to achieve various other beneficial results.

According to a first aspect of the invention there is provided a substance or composition for use in a method of treatment of human and animal subjects to enhance the methylation capacity of such human or animal subjects, which substance or composition comprises L-methionine.

More specifically, there is provided a substance or composition for use at a dosage rate of 20 mg–90 mg L-methionine per kilogram body mass per day in a method of treatment of human subjects to enhance the methylation capacity of the subjects, an active ingredient of which is selected from the group consisting of L-methionine and its biologically acceptable salts.

The active ingredient may preferably be present in a quantity to provide a dosage rate of 20 mg–70 mg L-methionine per kilogram body mass per day. This means that the active ingredient is preferably present in a quantity to provide a dosage rate of 1,5 g–5,0 g L-methionine per day for a human subject of 40 kg–100 kg body mass.

The invention is also particularly applicable to animal subjects. Thus there may be provided in accordance with the invention a substance or composition for use at a dosage rate of 0,5 mg–100 mg L-methionine per kilogram body mass per day in a method of treatment of animal subjects to enhance the methylation capacity of the subjects, an active ingredient of which is selected from the group consisting of L-methionine and its biologically acceptable salts.

Because the enhancement of the methylation capacity of human and animal subjects has important consequences for various other functions or conditions in the human or animal body, as will appear more fully later on, the substance or composition according to the invention may be used in the treatment of various specific deficiencies and to achieve various specific beneficial results.

Thus, according to one aspect of the invention there is provided a substance or composition for use in a method of treatment of human or animal subjects to enhance the immune response system of such subjects, which substance or composition comprises L-methionine in an effective amount to provide a suitable daily dosage rate. The daily dosage rates for both human and animal subjects will generally be the same as set out above in respect of the enhancement of the methylation capacity of the humans and animals.

The substance or composition of the invention is thus particularly suitable for use in a method of treating human or animal subjects to correct immunological deficiencies of such subjects.

Because the substance or composition according to the invention has the effect of enhancing the immune response system and correcting immunological deficiencies of human and animal subjects, the substance or composition is also particularly effective for use in a method of treating human or animal subjects to combat viral infections of such subjects.

Without wishing to be bound to a theoretical explanation, the Applicants believe that a low methylation capacity in human or animal subjects may result in an impaired immune system.

The immune reaction system may be divided into a cellular and a humoral response. The cellular immune response is mediated mainly by the T-cell lymphocytes and the humoral immune response is determined by the B-cell lymphocytes. B-cell lymphocytes produce antibodies in response to foreign molecules (antigens) which antibodies enable the T-cell lymphocytes to recognise the antigens thereby facilitating the destruction or removal of these antigens from the body.

The Applicants believe that a decline in the methylation capacity of the body may lead to a severe impairment of the production of T-cells and B-cells. It would appear that the T-cell function may be the most susceptible to a low methylation capacity.

The Applicants believe that by enhancing or increasing the methylation capacity of the body the immune response may be activated or enhanced. The Applicants have found that if a substance or a composition comprising or containing an effective amount of L-methionine as the active ingredient is administered to a human or an animal subject, this has the effect of increasing or enhancing the methylation capacity and thus of activating or enhancing the immune response.

L-methionine (L-met) is a naturally occurring amino acid which carries a methyl group which group may be rendered transferable to a large variety of other substances, e.g. as occurs in the transmethylation pathway in the human or animal body. The methyl group of L-methionine is not readily directly transferable to other substances but becomes readily transferable if first activated by converting the L-methionine to S-adenosylmethionine (SAM). The conversion facilitates the transferral of the methyl group. This conversion process is carried out in the metabolic methionine adenosyltransferase enzyme system of the human or animal body, and appears to be dependent also on other factors, such as the presence of adenosine triphosphate and magnesium and potassium ions. The Applicants believe that S-adenosylmethionine may be considered as the major methyl group donor in all living systems. The transfer of methyl groups in living systems, termed transmethylation, is essential for the functioning of a large number of biochemical processes.

When the S-adenosylmethionine releases its methyl group, it is converted to S-adenosylhomocysteine (SAH). In healthy human beings the ratio of S-adenosylmethionine to S-adenosylhomocysteine is approximately 20:1. In human beings suffering from severe immune deficiency, this ratio may decline considerably, for example, to a value as low as 5:1. Accordingly, an objective of the invention is to increase the ratio of S-adenosylmethionine to S-adenosylhomocysteine by administering to a subject L-methionine which is converted to S-adenosylmethionine by way of the methionine adenosyltransferase enzyme system referred to above.

The Applicants believe that it is essential that the L-isomeric form of methionine should be used in accordance with the invention. The use of a combination of the L- and D-forms is expected to be less effective, and in fact even detrimental, as the D-methionine may have an inhibitory effect on the L-methionine metabolism.

The Applicants believe that the D-isomeric form of methionine is unsuitable to be used in accordance with the invention, and that the use of D-methionine may in fact have seriously detrimental effects in the human or animal body. The Applicants believe that D-methionine is oxidatively deaminated by the enzyme deamino acid oxidase. This enzyme is expressed mainly in the kidneys, where it deaminates D-methionine to its ketoacid, which in turn is transaminated to L-methionine. However, a product of the oxidative deamination is hydrogen peroxide, and should a high concentration of the peroxide be allowed to build up in the kidneys, the kidneys may be damaged.

Secondly, should a D, L-mixture of methionine be used, the Applicants believe that the enzyme S-adenosyltransferase may bind also with the D-methionine, so that the D-methionine would provide inhibitive competition to the L-methionine in the methyl transfer phase.

The effective ingredient L-methionine may be produced by appropriate methods, such as by chemical synthetic processes and further separation of the D, L-methionine produced to yield the required L-methionine. Alternatively, L-methionine may be produced by protein lysis and amino acid separation.

According to a further feature of the invention, the substance or composition comprising L-methionine may contain at least one additive selected from the group consisting of biologically acceptable magnesium compounds, folic acid and analogues thereof, vitamin B6 and vitamers thereof, and vitamin B12 and vitamers thereof. The additives may be selected e.g. to enhance the conversion of L-methionine to S-adenosylmethionine, or to promote the conversion of homocysteine to L-methionine (as explained more fully below), or for other purposes.

For example, the additive may be a biologically acceptable magnesium compound selected from the group comprising biologically acceptable inorganic magnesium salts and magnesium chelates, the ratio by mass of the magnesium compound to L-methionine or its salt being between about 1:2 and 1:6 inclusive. The magnesium compound may for example be magnesium chloride or magnesium carbonate. Magnesium carbonate may be used where magnesium chloride is inconvenient to use by reason of its hygroscopic properties, e.g. where the composition is to be supplied in the form of a capsule. In order to provide a particulate or pulverulent substance with suitable flow characteristics, e.g. for filling capsule cases, magnesium carbonate and other suitable free flowing additives such as magnesium stearate, may be added.

The substance or composition may include the further additive folic acid in a ratio by mass of folic acid to L-methionine of 1:75–1:8000, e.g. in an amount to supply to a subject between about 0,7 µg and 0,3 mg inclusive of folic acid per kilogram body mass per day when the substance or composition is administered in a prescribed daily dosage.

The amount of folic acid to be incorporated in the substance or composition varies within wide ranges, and the preferred amount would depend in part on the nutritional state of the subject.

The substance or composition may further include vitamin B6 as an additive, in a ratio by mass of vitamin B6 to L-methionine of 1:60–1:3000, e.g. in an amount to supply to a subject between about 7 µg and 1,4 mg inclusive of vitamin B6 per kilogram body mass per day when the substance or composition is administered in a prescribed daily dosage. The vitamin B6 may be provided in the form of pyridoxine. The substance or composition may preferably also include vitamin B12 as an additive, in a ratio by mass of vitamin B12 to L-methionine of 1:60 000–1:300 000, e.g. in an amount to supply to a subject between about 0,1 µg and 100 µg inclusive of vitamin B12 per day when the substance or composition is administered in a prescribed daily dosage. The vitamin B12 may be provided in the form of cyanocobalamin.

It is preferred, in accordance with the invention, for the substance or composition to include, in addition to the L-methionine as hereinbefore set out, also all of the further additives comprising a pharmaceutically acceptable magnesium compound, folic acid or a folate, vitamin B6 and vitamin B12. Thus, there may be provided a substance or composition in accordance with the invention which includes at least one additive but preferably all of the additives selected from the following group, namely a biologically acceptable magnesium compound selected from the group consisting of biologically acceptable inorganic magnesium salts and magnesium chelates, the ratio by mass of the magnesium compound to L-methionine being 1:2–1:6;

folic acid in a ratio by mass of folic acid to L-methionine of 1:75–1:8000;

vitamin B6 in a ratio by mass of vitamin B6 to L-methionine of 1:60–1:3000; and vitamin B12 in a ratio by mass of vitamin B12 to L-methionine of 1:60 000–1:300 000.

It should be understood, however, that one or more of the additives may also be administered separately, e.g. in the form of a separate composition to be administered simultaneously with the L-methionine containing composition. The additives may also be supplied to a subject as part of the usual intake of minerals and vitamins.

On the basis of the parameters set out above, there may be provided a substance or composition for use as a daily dosage in a method of treatment of human subjects to enhance the methylation capacity of the subjects, which includes the following components in the following proportions:

L-methionine 1,5–5 g

Magnesium chloride 250–2500 mg

Magnesium carbonate 30–120 mg

Folic acid 0,6–20 mg

Vitamin B6 1,5–25 mg

Vitamin B12 15–25 µg

The Applicants believe that the invention may advantageously be used in the treatment of allergies in humans. It is believed that the release, turnover and homeostasis of histamine play an important role in the symptomatic field of allergies. The accumulation of histamine in specific tissues of the body may lead to an aggravation of the allergic reaction. The Applicants believe that the substance or a composition may be used for the treatment of human and animal subjects to facilitate the breakdown or inactivation of histamine in such human or animal subjects. The Applicants believe that by facilitating the breakdown of histamine in accordance with the invention it may be possible to suppress allergic reactions, or at least reduce the symptoms of allergic reactions.

It is believed that the breakdown of histamine is controlled by two enzymes, namely histaminase and histamine N methyl transferase.

It is believed that histaminase is produced in the liver and secreted into the plasma where it breaks down histamine in the presence of oxygen to imidazole acetaldehyde. The full activity of histaminase is dependent on the presence of magnesium ions (such as from magnesium chloride). Accordingly, when it is intended to treat the allergic reaction of a human subject, a suitable magnesium compound would preferably be an additive to the composition or formulation in accordance with the invention.

The Applicants have found, surprisingly, that by administering a substance or composition containing L-methionine in accordance with the invention to a human subject suffering from a deficiency in histaminase production, the histaminase levels are increased considerably, in some cases as much as threefold. Although the reason for this increase is not fully understood, clinical tests have shown that such an unexpected increase in histaminase levels occurs.

Furthermore, it is believed that histamine N methyl transferase methylates histamine to methyl histamine. Methyl histamine is generally inactive in respect to the allergic process. The histamine N methyl transferase uses a cosubstrate S-adenosylmethionine as a methyl donor. If the methylation capacity of humans or animals is low, then the turnover rate of histamine N methyl transferase may be insufficient. Because the Applicants' invention will have the effect of increasing the methylation capacity of human or animal subjects, so as to increase the concentration of S-adenosylmethionine, it is believed that the Applicants' invention will also suppress the symptoms of the allergic reaction by preventing the accumulation of histamine. Because the presence of magnesium ions is necessary for the full activity of histaminase, the invention envisages to provide magnesium ions together with L-methionine (methyl donor) to enhance the enzyme system involved in the breakdown of histamine.

One of the most common symptoms of persons suffering from an allergic condition is allergic rhinitis. The symptoms may include sneezing, pruritis and rhinorrhoea.

Clinical manifestations include that the turbinates of the nasal septum may be swollen, and the mucus may be pale or mauvish.

In a clinical test carried out on three patients suffering from allergic conditions and disclosing the clinical symptoms set out above, it was found that treatment over a period of 10 days with a composition in accordance with the invention, administered to the patients to provide a daily dosage rate of 3 g L-methionine as set out below, gave the following results when histaminase levels were measured before and after treatment:

COMPOSITION IN DAILY DOSAGE

L-methionine 3 g
Magnesium chloride 600 mg
Folic acid 8 mg
Vitamin B6 10 mg
Vitamin B12 20 µg

RESULTS

The plasma enzyme histaminase levels were determined by a highly specific procedure using histamine as a substrate, at the beginning of the treatment and after 10 days, and the following results were obtained:

Patient 1: Before treatment—<0.3 units/l plasma
After 10 days of treatment—1 units/l plasma
Patient 2: Before treatment—<0.3 units/l plasma
After 10 days of treatment—1.8 units/l plasma
Patient 3: Before treatment—0.303 units/l plasma
After 10 days of treatment—1.82 units/l plasma Clinical observation of the patients showed positive clinical images. A reduction in the swelling of the mucous membranes was observed, and a colour change of the mucus to normal. The post-nasal drip ceased, and the chronic rhinitis was reduced. The air passages were opened, and sneezing and watering of the eyes disappeared.

The Applicants believe that the substance or composition may also be effective in treating patients infected with various viral diseases. The viral diseases may include diseases caused by the human immunodeficiency virus (HIV), Coxsackie virus, Epsteinbarr virus ("Yuppie-flu"), and other viral diseases such as influenza, measles, etc. The substance or composition may also be an effective supplement with anti-microbials against bacterial infections as in the case of tuberculosis, and other microbiological diseases. The substance or composition may be administered in conjunction or in combination with other medicinal treatment agents to enhance or increase the effectiveness of said treatment, such as analgesics, anti-inflammatory agents, antipyretics, antibiotics, etc.

The ailment thought by some to be caused by the Epsteinbarr virus, known as Chronic Fatigue Syndrome or Yuppie-flu, reveals a syndrome of chronic fatigue. Medically it is poorly defined, and involves chronic and recurrent fatigue and various combinations of other symptoms such as sore throat, lymphnode tenderness, headache and myalgia.

Laboratory tests are not generally useful in uncovering previously undetected conditions, or in determining the cause of the fatigue. It is thought that a viral infection may contribute to the condition in a certain percentage of patients.

A variety of treatments have been tried, but without success. These include the administration of antidepressants and antiviral drugs.

The immune system is believed to involve a specific ratio between the CD4 and CD8. T-lymphocytes (the CD4 cells being the helper/inducer cells, and the CD8 cells 10 being the suppressor cells). The ratio of CD4:CD8 T-lymphocytes in healthy persons is about 1,6–2,2. In many acute viral infections this ratio falls temporarily both as a result of the decrease of the helper/inducer cells (CD4), and the increase of the suppressor/cytotoxic cells (CD8).

The Applicants have found that patients suffering from chronic fatigue syndrome and treated with the substance or composition according to the invention, showed a noticeable recovery within 20 days. Tests disclosed that in those cases where the CD4:CD8 ratio was impaired, the normal ratio of CD4:CD8 T-lymphocytes was restored.

A composition according to the invention was administered to eight patients suffering from chronic fatigue syndrome, in twice daily doses, the composition for a total daily dosage consisting of the following components in the following proportions:

L-methionine 3 g
Magnesium chloride 600 mg
Magnesium carbonate 100 mg
Folic acid 8 mg
Vitamin B6 10 mg
Vitamin B12 20 µg The results are set out below, and the clinical observations are shown. In the case of patient no VII T-lymphocyte counts were recorded after a 10 month interval, and a significantly increased CD4:CD8 cell ratio was disclosed.

I MALE CAUCASIAN 65 YEARS

Diagnosis: Fatigue syndrome since August 1991
Clinical
results: Main complaints—fatigue and malaise both disappeared after five days of treatment. No side effects.

II FEMALE CAUCASIAN 58 YEARS

Diagnosis: Fatigue syndrome since 1991
Clinical
results: Improved fatigue and myalgia after 21 days of treatment. Mood improvement was also reported.

III FEMALE CAUCASIAN 29 YEARS

Diagnosis: Fatigue syndrome since December 1991

Clinical
results: Improved fatigue, mood lifting and more energy after 12 days of treatment. Previously painful cervical glands—pain disappeared.

IV MALE CAUCASIAN 43 YEARS

Diagnosis: Fatigue syndrome since early 1991

Clinical
results: Improved fatigue, mood lifting, more energy, reduced malaise and myalgia after 21 days of treatment.

V MALE CAUCASIAN 75 YEARS

Diagnosis: Fatigue syndrome since 1991

Clinical
results: Improved fatigue after 10 days of treatment.

VI MALE CAUCASIAN 6 YEARS

Diagnosis: Fatigue syndrome since 1990

Clinical
results: Mood improvement, more energy, glands less painful after 14 days of treatment. Lymphocytes cell counts return to normal, ie from a previous low of 1,5 to 3,85.

VII FEMALE CAUCASIAN 47 YEARS

Diagnosis: Fatigue syndrome since March 1991

Clinical
results: Improved fatigue symptoms after 21 days. First lymphocyte counts were made on 23 March 1991. Second lymphocyte counts were made on 17 January 1992. CD4: Lymphocytes improved from 36% to 51% CD4:CD8 ratio improved from 0,7 to 2,0. The lymphocyte counts are set out in Tables 1 and 2 below.

VIII FEMALE CAUCASIAN 43 YEARS

Diagnosis: Fatigue syndrome since mid 1991

Clinical
results: Fatigue improved, more energy, mood improvement and sleep pattern improvement after 12 days of treatment.

TABLE 1

FIRST LYMPHOCYTE COUNT

| LYMPHOCYTE SUBSETS | RESULTS | RANGES |
|---|---|---|
| Total Lymphocyte count | 1452/cmm | 1000–4000 |
| Total T-cell count | 1278/cmm | 750–2700 |
| Helper (CD4+) cell count | 523/cmm | 600–1500 |
| Helper (CD4+) cell % | 36% | 30–60 |
| Suppressor (CD8+) cell count | 711/cmm | 400–1000 |
| CD4+:CD8+ ratio | 0,7 | 1,0–2,0 |
| Natural KILLER cells | 131/cmm | 50–1160 |
| Natural KILLER cells % | 9% | 5–29 |
| B-cells | 87/cmm | 70–920 |

REMARKS

Chronic fatigue syndrome (myalgic encephalomyelitis, low natural killer cell disease, chronic fatigue with immune disorder syndrome) may be associated with a variety of immunological disorders.

T-cell numbers range from normal to a CD4+:CD8+ratio of<1.

Functional T-cell abnormalities are common, particularly overproduction of cytoxins such as Interleukin 2.

Natural killer cell numbers may be low and/or functionally suppressed.

A normal distribution of lymphocyte subsets does not necessarily exclude a diagnosis of CFS in patients who meet the strict clinical criteria for this condition.

TABLE 2

SECOND LYMPHOCYTE COUNT

| LYMPHOCYTE SUBSETS | RESULTS | UNITS | RANGES |
|---|---|---|---|
| CD4 - Helper cells: | | | |
| Patient | 51 | % | 49–71 |
| Control | 58 | % | 49–71 |
| CD8 - Suppressor cells: | | | |
| Patient | 25 | % | 19–41 |
| Control | 30 | % | 19–41 |
| Other - B & NK cells: | | | |
| Patient | 24 | % | 8–15 |
| Control | 12 | % | 8–15 |
| Ratio CD4:CD8: | | | |
| Patient | 2,0 | % | 1,2–3,6 |
| Control | 1,9 | % | 1,2–3,6 |

REMARKS

The CD4:CD8 ratio of patients who test HIV positive, is proportionate to the immune defect, and may be utilised to monitor the progress of the disease. The normal CD4:CD8 ratio is between 1,2:1 and 3,6 1.

The Applicants believe that the substance or composition according to the invention may also be suitable for treating various other conditions or deficiencies related to the immune system of human or animal subjects. Thus the substance or composition may be used for treating human or animal subjects, to stimulate bone marrow to produce B-lymphocytes in said subjects, to stimulate B-cell production. In similar manner, the bone marrow may be stimulated to produce the necessary precursors of T-lymphocytes, to produce T-cells.

The Applicants believe that a substance or composition, or a formulation comprising L-methionine as an active ingredient, may be used in a method of treatment where the patient is suffering from Acquired Immunodeficiency Syndrome (AIDS). The Applicants believe that the substance or composition may halt or prolong the onset of AIDS. The advantage of using the said substance or composition is that it comprises natural compounds that are generally non-toxic if used in prescribed dosages. In other words, according to the invention there is provided a natural non-toxic enhancement of the immune system.

Tests are being conducted with patients infected with the HI virus, to determine whether the substance or composition according to the invention, when administered to the patients, in accordance with the invention, will have an immuno-stimulating effect to increase the levels of the CD4 and CD8 T-lymphocytes. At the same time clinical observations are made to determine whether any relief of symptoms and/or other beneficial effects can be observed.

A composition according to the invention is administered to the patients in twice daily doses, the composition in total daily dosage consisting of the following ingredients in the following proportions:

L-methionine 3 g

Magnesium chloride 600 mg

Magnesium carbonate 100 mg

Folic acid 8 mg

Vitamin B6 10 mg

Vitamin B12 20 µg

RESULTS

Although the biochemical results are still inconclusive, the clinical observations were favourable, and all the patients felt more energetic and endured less discomfort.

Furthermore, no negative side effects were observed.

In accordance with the principles of the invention, as set out above, a substance or composition to be used in a treatment of animal subjects to enhance their methylation capacity may likewise include at least one additive selected from the group consisting of biologically acceptable magnesium compounds, folic acid and analogues thereof, vitamin B6 and vitamers thereof, and vitamin B12 and vitamers thereof.

In one embodiment, such a substance or composition for use with animals, may include at least one additive selected from the following group, namely a biologically acceptable magnesium compound selected from the group consisting of biologically acceptable inorganic magnesium salts and magnesium chelates, the ratio by mass of the magnesium compound to L-methionine being 1:2–1:8;

folic acid in a ratio by mass of folic acid to L-methionine of 1:100–1:4000;

vitamin B6 in a ratio by mass of vitamin B6 to L-methionine of 1:50–1:2000; and vitamin B12 in a ratio by mass of vitamin B12 to L-methionine of 1:20 000–1:800 000.

The substance or composition in accordance with the invention may be used for treating a variety of animals to enhance their methylation capacity and to achieve the other beneficial results as set out herein, namely to poultry (including turkeys and other Gallinaceous birds), ostriches, birds held in captivity in aviaries, horses, pigs, and other fast-growing ruminant and non-ruminant animals.

The term "animals" will be used herein to denote generally all of the animals referred to above, ie poultry (including turkeys and other gallinaceous birds), ostriches, birds held in captivity, horses, pigs, and other fast-growing ruminant and non-ruminant animals.

The animals with which the invention is concerned are often susceptible to a variety of diseases and pathological conditions, which the Applicants believe are linked to skeletal, metabolic and immunological deficiencies caused by certain nutrient deficiencies. Thus, horses are often prone to injuries of their ligaments, and they often suffer from colic. Animals sometimes generally have a weak immune system leading to a variety of infections and often to sudden death. Finally, many animals, and particularly ostriches and horses, often display anxiety and stress-related behaviour.

The Applicants believe that the advantages of the invention may be applied with great benefit to reduce or at least relieve the diseases and deficiencies referred to above.

When the substance or composition according to the invention is to be administered to ruminants, it may be necessary to incorporate the substance or composition in a suitable formulation so as to by-pass the rumen. It has been found that milk provides a suitable carrier; alternatively, the substance or composition may be encapsulated in a capsule.

Specifically there may be provided a substance or composition for use in a daily dosage of 0,04 g per kilogram body mass in a method of treatment of ostriches to enhance the methylation capacity of the ostriches, which includes the following components in the following proportions:

L-methionine 1–4 kg

Magnesium chloride 500 g–2 kg

Folic acid 1 g–10 g

Vitamin B6 2–20 g

Vitamin B12 5–50 mg

It is known amongst persons concerned with the breeding of ostriches, that it is difficult successfully to breed and raise ostriches. Ostrich eggs are often infertile and only a small percentage of ostrich eggs will normally hatch. The mortality amongst ostrich chicks, particularly very young ones, is also very high, and a large percentage of those chicks that do hatch will die before they reach maturity, often before they reach the age of three months.

The high mortality is due to a variety of diseases and pathological conditions, which the Applicants believe are linked to skeletal, metabolic and immunological deficiencies caused by certain nutrient deficiencies. Thus, the young chicks often have extremely weak legs and lax joints, and their ligaments are prone to injury; they often suffer from connective tissue diseases, and anal prolapses often occur. They also generally have a weak immune system leading to a variety of infections and often to sudden death. Finally, young ostrich chicks are notorious for their anxiety and stress-related behaviour.

Even those ostrich chicks that do survive an early death are susceptible to a variety of diseases and to the conditions referred to above. Because ostrich chicks are extremely fast-growing (they can grow within one year from a body weight of 0,5 kg at the time of hatching to 160 kg), these defects are exacerbated. The Applicants believe that many of these problems can be avoided or at least mitigated by the provision of a nutritive supplementation of or a treatment with a substance or composition in accordance with the invention.

In a particular application, the substance or composition may also be used for treating poultry for stimulating the bursa of fabricius to produce B-cell lymphocytes and B-cells, to enhance the immune resistance of the poultry. This aspect is of particular importance in regard to the battery rearing of chickens where the chickens are exposed to a variety of viral and other infections.

According to a further aspect of the invention, the substance or a composition may be used for the treatment of human and animal subjects to stimulate creatine production of such human or animal subjects. It is believed that creatine levels play an important part in muscle development. Accordingly, the Applicants believe that the invention in this regard would be of particular utility in the rearing of race horses.

According to another aspect of the invention, the substance or a composition may be used for the treatment of human and animal subjects to facilitate the breakdown of adrenalin and noradrenalin in such human or animal subjects. Applicants believe that regulation or enhancement of the breakdown of adrenalin and noradrenalin may have important implications in the treatment of hyperactivity in children, and anxiety and stress-related behaviour in animals, e.g. in ostriches and race horses.

According to another aspect of the invention, there is provided a method of enhancing the methylation capacity of human subjects, which includes the step of administering to a subject a substance or composition according to the invention, is an effective amount, being a daily dosage to supply to the subject 20 mg–70 mg L-methionine per kilogram body mass.

Further according to the invention there is provided a method of enhancing the methylation capacity of animal subjects, which includes the step of administering to a subject a substance or composition according to the invention, in an effective amount, being a daily dosage to supply to the subject 10 mg–50 mg L-methionine per kilogram body mass.

The method according to of the invention may also be applied to enhance the immune response system of the human and animal subjects, and to correct immunological deficiencies. The daily dosage rates for achieving the desired result will generally be the same as those set out in regard to the enhancement of the methylation capacity, since many of the beneficial results will flow from an improved methylation capacity.

The Applicants believe that the method of treatment according to the invention is effective to enhance the immune response of subjects, since it is able to stimulate the bone marrow to produce the necessary precursors of T-lymphocytes and B-lymphocytes, and the T-cells and B-cells themselves. When applied to poultry, the method is able to stimulate the bursa of fabricius to produce B-cell lymphocytes.

The method according to the invention therefore is particularly effective for treating human or animal subjects to combat viral infections. As mentioned before, the viral infections are not only those causing diseases such as influenza, measles, chronic fatigue syndrome ("Yuppie-flu") and the like, but also infections by the human immunodeficiency virus (HIV) in persons suffering from AIDS.

Furthermore, as mentioned before, the invention is also particularly suitable for treating viral infections in poultry, and for enhancing the immune resistance to viral infections in poultry, e.g. in the case of battery reared chickens.

According to a further feature of the invention, the method has been found to be effective in treating an allergic response in human subjects.

The reason why treatment by the method according to the invention would have the effect of suppressing an allergic response, is to be found in the fact that the substance or composition of the invention is able to facilitate the breakdown or inactivation of histamine production, in the manner as already explained before.

The method of treatment according to the invention may also be used for treating human or animal subjects to increase creatine production, with the beneficial effect thereof on muscle development.

Finally, the method of treatment of the invention may be used for treating human or animal subjects to facilitate the breakdown of adrenalin and noradrenalin, the beneficial result of which is that anxiety, hyperactivity and stress-related behaviour may be controlled.

It is also envisaged, in accordance with the invention, to provide a formulation to be administered to human subjects, at a dosage rate of 20 mg–70 mg L-methionine per kilogram body mass per day to enhance the methylation capacity of the subjects, which consists of a substance or composition according to the invention, and a biologically acceptable carrier.

Similarly, a formulation may be provided to be administered to animal subjects at a dosage rate of 10 mg–50 mg L-methionine per kilogram body mass per day to enhance the methylation capacity of the subjects, which consists of substance or composition in accordance with the invention, and a biologically acceptable carrier.

As set out before, the formulations may be administered to human or animal subjects to enhance the immune response system of such subjects, and to correct immunological deficiencies, and to combat viral infections of such subjects.

As explained before, the formulation may be administered to human or animal subjects to stimulate bone marrow production of B-lymphocytes and T-lymphocytes, and B-cells and T-cells.

The formulation may also be useful for combatting or controlling an allergic response in human subjects, in the manner explained before.

Other beneficial results that may be achieved by administering the formulation to human and animal subjects, include increasing creatine production, and facilitating the breakdown or inactivation of adrenalin and noradrenalin.

In making up and administering these formulations, an effective amount of the substance or composition is understood by those skilled in the art to mean that a sufficient amount of the substance or composition is provided such that upon administration to the human or animal by the chosen route, for example the oral route, sufficient active ingredients will be provided on each administration to supply to the subject the indicated dosage rate, so as to give the desired result. However, the effective amount of the active ingredients should be at a level that is not toxic to the human or animal during the term of treatment.

In view of the variety of uses of the substance or composition of the invention, it must be appreciated that the substance or composition may be administered in various forms and by various routes, e.g. orally, subcutaneously, intramuscularly, intravenously etc, and therefore the substance or composition may be provided in the form of a suitable liquid or solid formulation.

The formulation may include one or more further additives selected e.g. to enhance the efficacy of the active ingredient, or to achieve other beneficial results. Thus the formulation may include a pharmaceutically acceptable magnesium, folic acid, vitamin B6 and vitamin B12, all in pharmaceutically acceptable amounts as hereinbefore set out.

A formulation according to the invention may thus be provided, to be administered to human subjects at a dosage rate of 20 mg–70 mg L-methionine per kilogram body mass per day, which formulation includes the following components in the following proportions:

L-methionine 1,5–5 g

Magnesium chloride 250–2500 mg

Magnesium carbonate 30–120 mg

Folic acid 0,6–20 mg

Vitamin B6 1,5–25 mg

Vitamin B12 15–25 µg and a biologically acceptable carrier.

Similarly a formulation may be provided to be administered to animal subjects at a dosage rate of 10 mg–50 mg L-methionine per kilogram body mass per day, which formulation includes the following components in the following proportions:

L-methionine 1–4 kg

Magnesium chloride 500 g–2 kg

Folic acid 1–10 g

Vitamin B6 2–20 g

Vitamin B12 5–50 mg and a biologically acceptable carrier.

The formulation for human subjects may conveniently provided in unit dosage form, each unit dose comprising 0,3 g–0,7 g of L-methionine. The unit dosage form may conveniently be a capsule. For animal subjects, the formulation may be provided in the form of a powder, to be dissolved in water to make up a liquid formulation.

Because the L-methionine has an unpleasant odour, it may be necessary to camouflage its presence with flavouring ingredients, such as bran or molasses for horses.

It is also possible to provide a formulation in the form of an injectable solution, in combination with a pharmaceutically acceptable diluent. Another possibility is to provide the substance or composition in the form of a food supplement, in combination with an edible carrier.

The invention extends in particular to a foodstuff formulation suitable to be used for ostriches, particularly young and breeding ostriches, which includes a supplement as described herein, in combination with a balanced feedmeal composition. Such a feedmeal composition may include mealies (maize), cut lucerne, wheat bran, fish meal, lime stone ($CaCO_3$), sun flower oil cake, and further additives such as vitamins, salt, etc. The relative proportion of the supplement to the rest of the composition nay be as set out above.

This invention extends also to a supplement for fodder suitable to be used for feeding poultry (including turkeys and other gallinaceous birds), ostriches, birds held in captivity, horses, pigs, and other fast-growing ruminant and non-ruminant animals. The invention relates also to a foodstuff formulation intended to be used for feeding these animals, and to a method of feeding these animals, particularly those that are young or breeding.

Figure 1:
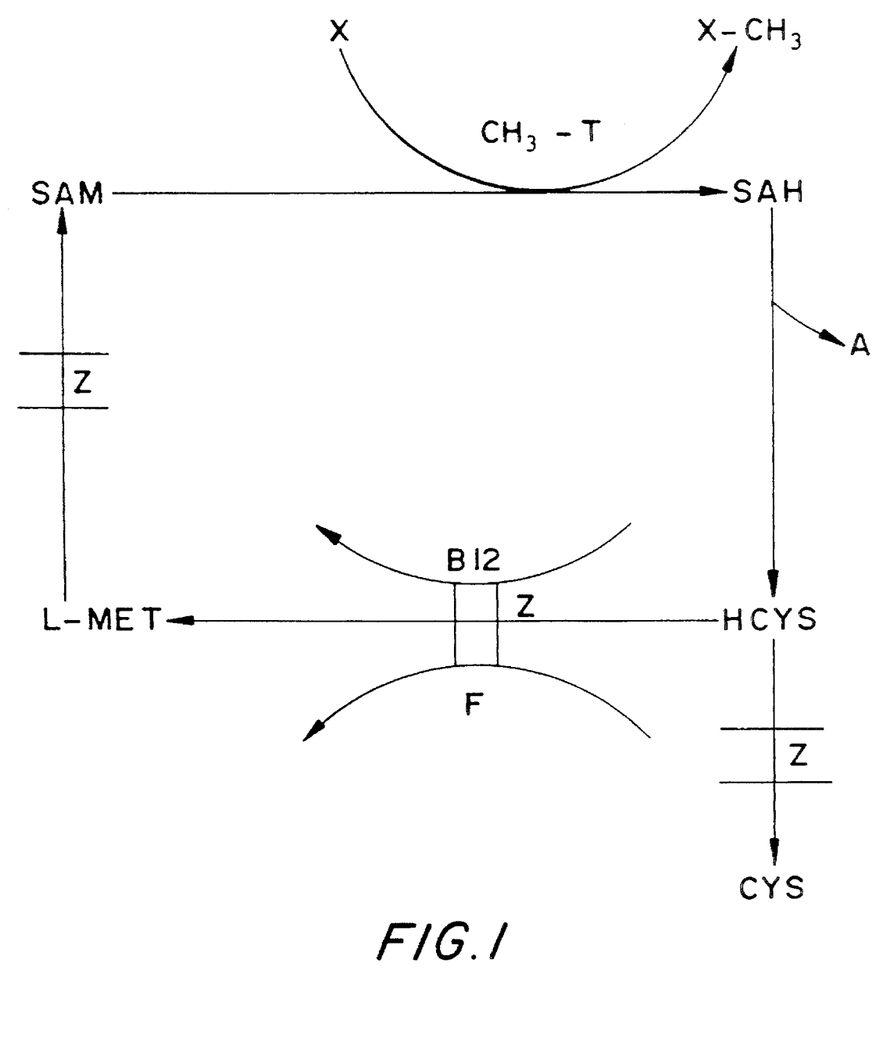
FIG. 1 shows a simplified flow diagram of the transmethylation pathway forming part of the metabolic methionine adenosyltransferase enzyme system. The letter symbols used therein have the following significance.

The invention, the manner in which it may be put into practice, and the manner in which the Applicants believe it to operate will now be further described by way of explanation and with reference to the schematic representation shown in the accompanying drawing.

BRIEF DESCRIPTION OF THE DRAWING

SAM—S-adenosylmethionine

SAH—S-adenosylhomocysteine

L-MET—L-methionine

HCYS—Homocysteine

CYS—Cysteine

A—Adenosine

X—Any compound to be methylated

X—$CH_3$—The compound X after methylation $CH_3$—T—The enzyme methyl transferase F—Folate B12—Vitamin B12

Z—A site in the transmethylation pathway where the transmethylation system may be inhibited.

The methyl group may be transferred from S-adenosylmethionine (SAM) to a compound X as indicated. The double lines designated Z indicate possible sites where the transmethylation pathway may be inhibited. If any of these sites are affected it may lead to a decrease in the formation of S-adenosylmethionine (SAM) and a consequent decrease in the methylation capacity of the body, and this may lead to a suppressed immune system. The Applicants believe that the transmethylation system may be inhibited or interfered with at sites in the pathway indicated by the reference Z; however, the Applicants do not intend to state that the utility of the invention is limited to only the sites marked Z as there may be additional places in the pathway where methylation may be affected.

By administering the substance or composition according to the invention with L-methionine as the active ingredient, the reduced methylation capacity of the body may be overcome or enhanced. It is believed that the presence of increased levels of L-methionine, preferably in combination with increased levels of $Mg^{++}$ ions, folate, and vitamins B6 and B12, will enable the transmethylation system to function more effectively by facilitating the transfer of the methyl group by the enzyme methyl transferase to the compound X.

It should be understood that the active ingredient L-methionine may be used without further additives if only short-term dosages are required to overcome the reduced methylation capacity. If a long-term dosage is required then additional additives are necessary to prevent an accumulation of intermediate products which may become toxic to the body. It should also be understood that some or all of the additives referred to herein may be supplied to a subject as independent nutritional components.

Thus, magnesium chloride may be added to the substance or composition to provide magnesium ions which may be necessary for the enzyme methionine adenosyltransferase to function. Folic acid (folate) and vitamin B12 (cyanocobalamin) may comprise further additives in order to facilitate the methylation of homocysteine to L-methionine. Folic acid may be intracellularly metabolised to form methyltetrahydrofolate which is an essential substrate for the methylation of homocysteine. If folic acid and vitamin B12 are not present, it may lead to an accumulation of homocysteine which may be detrimental to the body. High levels of homocysteine has been shown to cause arthrosclerosis. Vitamin B6 may be essential in the catalysis of homocysteine to form cysteine. The reaction is usually catalyses by the enzyme cystathion B synthetase and the enzyme cystathion lyase, which are dependent on the presence of vitamin B6.

In a field trial carried out with chickens it was found that by administering to chickens a substance or composition comprising L-methionine as the active ingredient, the immunological resistance of the chickens to certain viral diseases increased significantly, and that mortality rates over a six week growth period decreased. It was further shown that the humoral system (B-cells) could be stimulated to increase antibody production in response to certain viral infections, while the feed intake and cumulative weight gain of the treated chickens improved.

The trial was conducted on broilers and was carried out at the Animal and Dairy Science Research Station, Irene, Republic of South Africa.

Date of commencement of the trial was 28 Feb. 1992. It ran for 42 days.

The trial was divided into 4 tests split by sex giving 12 replications per treatment. The reason for splitting sexes was only to reduce competition during feeding, and results were not allocated per sex but per treatment. There were 48 pens with 10 birds per pen. Parameters measured in the trial were:

1. Cumulative mass gain
2. Cumulative feed intake
3. Weekly feed efficiency
4. Weekly mortalities 5. Bursa mass 6. IBD titres (Infectious Bursal Disease, ie Gumboro disease)

7. NCD titres (Newcastle Disease)

In certain parameters only pens with 8, 9 and 10 birds left at trial termination were used as it was found that the lowered stocking density (from high mortalities) affected growth.

A composition in accordance with the invention was made up as follows:

L-methionine 2,6 kg

Magnesium chloride 800 g

Folic acid 8 g

Vitamin B6 10 g

Vitamin B12 20 mg

The composition was added either to the solid feedstuff of the birds (treatment T2 and T4), or to the drinking water (treatment T3), so that a daily dosage of about 0,04 g per kilogram body mass was administered for the water treatment T3, and 0,12 g per kilogram body mass was administered for the feed treatments T2 and T4.

Treatments were as follows:

T1—control

T2—feed treatment (continued day 1–21)

T3—water treatment (continued day 1–21)

T4—feed treatment (continued day 1–42)

REMARKS:

1. With the water treatment T3 the entire daily dosage was taken in over about 1–2 hours (ie until the total daily ration of water was consumed). With the feed treatments T2 and T4 the daily dosage was taken in throughout the day (ie as the feed was consumed). It follows that the birds on water treatment T3 in fact received a bolus dosage of the active ingredient, and this had certain important results, as will appear below.

2. Treatments T1, T2 and T3 received the composition dosage for 21 days only, whereafter dosing was discontinued. T4 received the composition dosage for 42 days, ie until slaughter.

1) Cumulative mass gains

This parameter was measured in grams. Mass values at 3, 5 and 6 weeks were recorded (pens with 8 or more birds only). Day old starting mass values were excluded.

|    | Mass (grams) | | |
| --- | --- | --- | --- |
|    | 3 weeks | 5 weeks | 6 weeks |
| T1 | 533,1 | 1087,5 | 1401,8 |
| T2 | 536,4 | 1093,0 | 1444,7 |
| T3 | 520,7 | 1087,2 | 1430,8 |
| T4 | 521,6 | 1116,9 | 1465,8 |

Analysis of results

Week 3

The variations show no pattern, with T2 and T4 receiving the same treatment but showing extremes in growth rate. T3 shows the lowest rate recorded.

Week 5

T4 is superior to all other treatments. T3 shows poorest results but T1, T2 and T3 shows insignificant differences between them.

Week 6

T4 is superior to all treatments; T2 and T3 are superior to the control.

SUMMARY

It appears that in T3, palatability of water treatment reduces water intake (the L-methionine has an unpleasant sulphurous odour). This has a bearing on feed intake. As a result T3 gains slowly. There is an increased growth near the end allowing T3 to overtake T1. T4 is superior after 5 and 6 weeks, but was second to T2 in the first 3 weeks. Up to 3 weeks the treatments for T2 and T4 were identical. After 3 weeks T4 continued with treatment while treatment for T2 and T3 ceased. T4 shows improved mass gains over all other treatments (4,37% improvement over control).

2) Cumulative feed intakes

This was measured in identical pens to 1) above.

|    | Mass (grams) | | |
| --- | --- | --- | --- |
|    | 3 weeks | 5 weeks | 6 weeks |
| T1 | 862,1 | 2112,9 | 2920,6 |
| T2 | 866,2 | 2128,0 | 3001,7 |
| T3 | 852,6 | 2127,6 | 2993,0 |
| T4 | 862,0 | 2155,4 | 3056,8 |

Analysis of results

Week 3

During the first 3 weeks cumulative phase T3 shows the lowest intake. As explained in 1) above, palatability of water will affect water and consequentially also feed intakes. The other three treatments have similar intakes.

Week 5 and Week 6

T4 (ie with continued treatment for 42 days) is far superior to the other treatment groups T2 and T3 (with treatment limited to 21 days). T2 and T3 were in turn superior to the control T1.

SUMMARY

T4 birds were able to consume greater volumes of feed than the control. T2 and T3 showed little difference between treatments and were also superior to the control but not to the same degree as T4.

3) Weekly feed efficiency (non-cumulative)

Feed efficiency is defined as the mass added per unit of feed consumed.

|    | Efficiency (fraction of 1) | | |
| --- | --- | --- | --- |
|    | 3 weeks | 5 weeks | 6 weeks |
| T1 | 0,785 | 0,468 | 0,560 |
| T2 | 0,785 | 0,527 | 0,587 |
| T3 | 0,786 | 0,506 | 0,588 |
| T4 | 0,797 | 0,523 | 0,599 |

Analysis of results

Week 3

There is very little variation between treatment groups.

Week 5

T4 and T2 are very similar (both receiving identical treatments up to 3 weeks) and are superior to T3 by 0,02.

T1 is inferior to all groups, ie by 0,04 from T3 and 0,06 from T2 and T4.

Week 6

Very little difference between T2, T3 and T4. However, T1 is inferior to the other three treatments by 0,04.

SUMMARY

Treatment either by water or feed dosage improves efficiency by a factor of 0,04; ie 1 unit kg body mass of feed produces 40 grams extra body mass. 4) Weekly Mortalities (cumulative in all pens)

|    | Mortalities (%) | | | | | |
|----|--------|--------|--------|--------|--------|----------|
|    | 1 week | 2 week | 3 week | 4 week | 5 week | 6 week   |
| T1 | 5,0    | 0,0    | 0,0    | 0,0    | 0,8    | 3,4 weekly |
|    | 5,0    | 5,0    | 5,0    | 5,0    | 5,8    | 9,2 cum  |
| T2 | 5,8    | 1,7    | 0,8    | 0,0    | 0,0    | 0,9 weekly |
|    | 5,8    | 7,5    | 8,3    | 8,3    | 8,3    | 9,2 cum  |
| T3 | 2,5    | 0,8    | 0,9    | 0,0    | 0,0    | 0,0 weekly |
|    | 2,5    | 3,3    | 4,2    | 4,2    | 4,2    | 4,2 cum  |
| T4 | 2,5    | 0,0    | 2,5    | 0,8    | 0,0    | 0,9 weekly |
|    | 2,5    | 2,5    | 5,0    | 5,8    | 5,8    | 6,9 cum  |

Analysis of results

T1 and T2 had the highest cumulative mortalities. Next was T4 followed by T3. A reason for T3 having the lowest cumulative mortality is believed to be that the water soluble composition had rapid early effects on the viability and immune resistance of the birds, as opposed to birds receiving the composition in their feed.

All treatments (T2–T4) showed an improvement in mortality in the last week over the control group (ie mortality of 0,0–0,9% as against mortality of 3,4%).

It is also believed that the bolus dosage received by the birds of T3 (as explained above) has superior results over a constant dosage spread over time, as received by the birds of T2 and T4.

5) Bursa mass as % of body mass

T1 0,245

T2 0,250

T3 0,292

T4 0,219

It appears that T4 shows the smallest bursas. However, the uniformity of the bursal mass values as a percentage of body mass, expressed as the coefficient of variation around the mean (CV) is as follows:

CV (%)

T1 40,92

T2 34,41

T3 40,89

T4 16,92

This shows that as a group T4 showed controlled reaction and response to the vaccines and disease challenges (IBD especially but also NCD). T4 shows neither marked, exaggerated responses when challenged by IBD (as was seen in the other groups), nor does it disclose macroscopic evidence of bursal atrophy.

This bursal reaction is also born out in the actual antibody titres to IBD and NCD, as shown below.

6) IBD—Infectious Bursal Disease (Gumboro) titres

The ELISA standard antibody assay procedure was followed in carrying out the titres. Blood samples were taken every week, and the IgM fraction tested. The tests are specific for Gumboro and Newcastle disease. In the Gumboro assay, the birds were inoculated on day 20, and the inoculation was carried out by conventional methods.

|    | Min (22–29 days) | Max (42 days) |
|----|------------------|---------------|
| T1 | 0,460            | 1,315         |
| T2 | 0,438            | 0,764         |
| T3 | 0,450            | 0,858         |
| T4 | 0,438            | 0,637         |

All blood samples show a drop in maternal antibodies from day 1 to a lowest level at ±22 days. Thereafter, following actual field challenges and the body's necessity to produce antibodies, a rise in titres occurs. T4 shows the lowest rise in titres which coincides with the least increase in bursal size noted. Note also that T2–T4 had very lower mortalities as opposed to the control group which also had the largest in IBD antibodies.

7) NCD—Newcastle Disease titres.

The ELISA standard antibody assay procedure was followed, as explained above. The birds were inoculated on day 1.

|    | Min (22–29 days) | Max (42 days) |
|----|------------------|---------------|
| T1 | 0,522            | 1,315         |
| T2 | 0,354            | 1,325         |
| T3 | 0,373            | 1,338         |
| T4 | 0,522            | 1,613         |

T4 produces significantly higher levels of NCD antibodies when compared to T1–T3.

Analysis

It will be noted that T3 shows titre values consistently higher than T2 in both the IBD and NCD titres, although treatment of these groups were both discontinued after 21 days. The Applicants believe that the reason for this is that the bolus dosage given to T3 (as explained above) in fact retarded the decline in maternal antibodies which normally takes place over the first 7–14 days. Consequently, if the decline in maternal antibodies can be retarded until own antibody production reaches an effective level, the result would be a levelling of the sharp decline usually found in the immune resistance of chickens between days 7–14, and an overall improvement in the immune resistance of chickens.

From the cumulative mortalities figures, it will be observed that the group T3 showed the lowest overall cumulative mortality, and the lowest weekly mortality rate over weeks 4, 5 and 6. Again this is attributed to the bolus dosage given to birds of the T3 group by way of the water treatment. It will be evident that this has important commercial implications, since the economic loss in the case of mortality during the later weeks is much greater than mortality during the early weeks.

The Applicants believe that bolus dosage to chickens over the first few days, say 4 days, followed by a period of discontinued treatment until say day 19, followed again by bolus dosage for about 5 days from day 19 onwards (when the risk of Gumboro infection is greatest), would give favourable results in practise.

The Applicants have found that administering to a patient a relatively high bolus dosage of the substance or composition according to the invention over a limited period of time, for example about two weeks, at the commencement of the treatment, preferably followed by a sustained maintenance dosage on a lower dosage level and for a prolonged period of time, gives improved results in practice. The bolus dosage level may be determined on the basis of animal or human subject tolerance levels, and parameters such as T-cell function, S-adenosylmethionine levels, and individual enzyme activity levels. The maintenance dosage level may likewise be determined with reference to parameters such as T-cell functions, S-adenosylmethionine levels, and individual enzyme activity levels. In practice it has been found that the maintenance dosage level may be about 50%–75% of the bolus dosage.

The invention accordingly envisages a method of treatment of human subjects, in which the prescribed daily dosage is administered to a subject in equal doses twice daily prior to meals, and in which a bolus dosage is administered over a limited period of time at the commencement of the treatment, the bolus dosage being 30 mg–90 mg L-methionine per kilogram body mass, followed by a sustained maintenance dosage of 20 mg–70 mg L-methionine per day per kilogram body mass for the remainder of the treatment period.

Such a method of treatment, ie where an initial bolus dosage over a limited period is followed by a maintenance dosage over a prolonged period, is expected to be specifically beneficial in the treatment of subjects suffering from AIDS.

Adult human subjects suffering from an impaired or inadequate immune system may be treated in accordance with the invention, by administering to such subjects a daily dosage of a formulation comprised of the following ingredients:

L-methionine 2,6 grams per day
Magnesium chloride 800 mg per day
Folate 8 mg per day
Vitamin B6 20 mg per day
Vitamin B12 10 ug per day

We claim:

1. A method of treating myalgic encephalomyelitis known as chronic fatigue syndrome in a human subject, comprising administering to said subject a composition comprising:
   (a) an active ingredient which is selected from the group consisting of L-methionine and its biologically acceptable salts, in a daily dosage to supply to the subject 20 mg–70 mg L-methionine per kilogram body mass;
   (b) a biologically acceptable magnesium compound selected from the group consisting of biologically acceptable inorganic magnesium salts and magnesium chelates, the ratio by mass of the magnesium compound to L-methionine being 1:2–1:6;
   (c) folic acid in a ratio by mass of folic acid to L-methionine of 1:75–1:8000;
   (d) vitamin $B_6$ in a ratio by mass of vitamin $B_6$ to L-methionine of 1:60–1:3000; and
   (e) vitamin $B_{12}$ in a ratio by mass of vitamin $B_{12}$ to L-methionine of 1:60,000–1:300,000.

2. The method according to claim 1 wherein the composition is administered daily to said subject and the components of the composition are in the following amounts:

L-methionine 1.5–5 g
Magnesium chloride 250–2500 mg
Magnesium carbonate 30–120 mg
Folic acid 0.6–20 mg
Vitamin $B_6$ 1.5–25 mg
Vitamin $B_{12}$ 15–400 µg.

3. The method according to claim 1, further comprising the steps of
   (i) administering before a first meal on each day a composition comprising:
      (a) an active ingredient which is selected from the group consisting of L-methionine and its biologically acceptable salts, in a daily dosage to supply to the subject 20 mg–70 mg L-methionine per kilogram body mass;
      (b) a biologically acceptable magnesium compound selected from the group consisting of biologically acceptable inorganic magnesium salts and magnesium chelates, the ratio by mass of the magnesium compound to L-methionine being 1:2–1:6;
      (c) folic acid in a ratio by mass of folic acid to L-methionine of 1:75–1:8000;
      (d) vitamin $B_6$ in a ratio by mass of vitamin $B_6$ to L-methionine of 1:60–1:3000; and
      (e) vitamin $B_{12}$ in a ratio by mass of vitamin $B_{12}$ to L-methionine of 1:60,000–1:300,000;
   (ii) administering, a bolus dosage over a limited period of time at the commencement of the treatment, the bolus dosage being 30 mg–90 mg L-methionine per kilogram of body mass, and
   (iii) administering, before a second meal on each day, a composition comprising:
      (a) an active ingredient which is selected from the group consisting of L-methionine and its biologically acceptable salts, in a daily dosage to supply to the subject 20 mg–70 mg L-methionine per kilogram body mass;
      (b) a biologically acceptable magnesium compound selected from the group consisting of biologically acceptable inorganic magnesium salts and magnesium chelates, the ratio by mass of the magnesium compound to L-methionine being 1:2–1:6;
      (c) folic acid in a ratio by mass of folic acid to L-methionine of 1:75–1:8000;
      (d) vitamin $B_6$ in a ratio by mass of vitamin $B_6$ to L-methionine of 1:60–1:3000; and
      (e) vitamin $B_{12}$ in a ratio by mass of vitamin $B_{12}$ to L-methionine of 1:60,000–1:300,000.

4. A pharmaceutical composition for the treatment of myalgic encephalomyelitis known as chronic fatigue syndrome in a human subject consisting essentially of:
   (a) an active ingredient of the composition selected from the group consisting of L-methionine and its biologically acceptable salts, in a daily dosage to supply to the subject 20 mg–70 mg L-methionine per kilogram body mass;
   (b) a biologically acceptable magnesium compound selected from the group consisting of biologically acceptable inorganic magnesium salts and magnesium chelates, the ratio by mass of the magnesium compound to L-methionine being 1:2–1:6;
   (c) folic acid in a ratio by mass of folic acid to L-methionine of 1:75–1:8000;
   (d) vitamin $B_6$ in a ratio by mass of vitamin $B_6$ to L-methionine of 1:60–1:3000; and (e) vitamin $B_{12}$ in a ratio by mass of vitamin B12 to L-methionine of 1:60,000–1:300,000.

5. A pharmaceutical composition for the daily treatment of myalgic encephalomyelitis known as chronic fatigue syndrome in a human subject consisting essentially of the components of the composition in the following amounts:

L-methionine 1.5–5 g

Magnesium chloride 250–2500 mg

Magnesium carbonate 30–120 mg

Folic acid 0.6–20 mg

Vitamin $B_6$ 1.5–25 mg

Vitamin $B_{12}$ 15–400 μg and a biologically acceptable carrier.

6. A food supplement for the treatment of myalgic encephalomyelitis known as chronic fatigue syndrome in a human subject consisting essentially of:

(a) an active ingredient which is selected from the group consisting of L-methionine and its biologically acceptable salts, in a daily dosage to supply to the subject 20 mg–70 mg L-methionine per kilogram body mass;

(b) a biologically acceptable magnesium compound selected from the group consisting of biologically acceptable inorganic magnesium salts and magnesium chelates, the ratio by mass of the magnesium compound to L-methionine being 1:2–1:6;

(c) folic acid in a ratio by mass of folic acid to L-methionine of 1:75–1:8000;

(d) vitamin $B_6$ in a ratio by mass of vitamin $B_6$ to L-methionine of 1:60–1:3000; and (e) vitamin $B_{12}$ in a ratio by mass of vitamin $B_{12}$ to L-methionine of 1:60,000–1:300,000; together with an edible carrier.

\* \* \* \* \*